United States Patent [19]

Walsh

[11] Patent Number: 5,686,632
[45] Date of Patent: Nov. 11, 1997

[54] METHOD OF PRODUCING A TOCOPHEROL PRODUCT

[75] Inventor: Leo Walsh, Lisle, Ill.

[73] Assignee: Henkel Corporation, Plymouth Meeting, Pa.

[21] Appl. No.: 696,767

[22] Filed: Aug. 14, 1996

[51] Int. Cl.$^6$ .................................................. C07D 311/72
[52] U.S. Cl. ............................................................ 549/410
[58] Field of Search .................................................. 549/410

[56] References Cited

U.S. PATENT DOCUMENTS

| | | |
|---|---|---|
| 2,680,749 | 12/1954 | Cawley et al. . |
| 3,538,119 | 11/1970 | Grant . |
| 3,551,457 | 12/1970 | Ross . |
| 3,655,852 | 4/1972 | Koff et al. . |
| 4,870,196 | 9/1989 | Thorengaard . |
| 4,875,847 | 10/1989 | Wenger et al. . |
| 4,880,018 | 11/1989 | Graves, Jr. et al. . |
| 4,981,711 | 1/1991 | Kearns et al. . |
| 5,132,133 | 7/1992 | Huber et al. . |
| 5,148,821 | 9/1992 | Best et al. . |
| 5,262,190 | 11/1993 | Cunningham et al. . |
| 5,334,407 | 8/1994 | Donnelly et al. . |
| 5,397,587 | 3/1995 | Thompson et al. . |
| 5,407,661 | 4/1995 | Simone et al. . |
| 5,427,809 | 6/1995 | Donnely et al. . |
| 5,429,835 | 7/1995 | Wenger et al. . |
| 5,501,868 | 3/1996 | Collings et al. . |

FOREIGN PATENT DOCUMENTS

| | | |
|---|---|---|
| 866489 | 4/1961 | United Kingdom . |
| 1007161 | 10/1965 | United Kingdom . |
| 1114150 | 5/1968 | United Kingdom . |

OTHER PUBLICATIONS

*Encyclopedia of Polymer Science and Engineering*, vol. 11, p. 262–267, (J. Wiley & Sons, Inc., NY, NY 1988).

C.E. Capes, "Size Enlargement," *Encyclopedia of Chemical Technology*, vol. 21, pp. 77–105, (Kirk–Othmer, eds., John Wiley and Sons, Inc., NY, NY, 1983).

*Primary Examiner*—Nicky Chan
*Attorney, Agent, or Firm*—Ernest G. Szoke; Wayne C. Jaeschke; Martin G. Meder

[57] ABSTRACT

A process of producing a tocopheryl succinate powder is provided. The process forming a tocopheryl succinate powder into a plastic mass. The plastic mass is then allowed to cool whereupon its sets to a solid state. The solid mass can then be subjected to a size reduction to obtain a tocopherol succinate powder having a desirable particle size, e.g. not more than 5% by weight through a 120-mesh sieve and not more than 5% by weight retained on a 14-mesh sieve.

18 Claims, No Drawings

METHOD OF PRODUCING A TOCOPHEROL PRODUCT

FIELD OF THE INVENTION

The present invention relates to a method of producing a tocopheryl succinate having a desirable particle size.

BACKGROUND OF THE INVENTION

Tocopherol compounds, also designated as vitamin E, are active components in vegetable oils. Vitamin E activity refers to the physiological activity of this group of nutrient materials. Materials having a vitamin E activity all belong to a distinct series of compounds which are all derivatives of chroman-6-ol. These compounds are all tocol derivatives having an isoprenoid C16-sidechain. The term "tocol" is used to mean 2-methyl-2-(4',8',12'-trimethyltridecyl)chroman-6-ol. These compounds are alpha-, beta-, gamma-, and delta-tocopherol, and are of primary importance for vitamin E activity. Of these, alpha-tocopherol has the highest vitamin E activity and is the most valuable.

Such naturally occurring tocopherol homologues are generally isolated from natural products such as vegetable oil sources by various combinations of procedures such as esterification, saponification, extraction, distillation, ion exchange, adsorption chromatography, precipitation of sterols, and crystallization. The tocol concentrate isolated will vary depending on the particular separation technique used in addition to the vegetable source. One such concentrate, for example, contains mixtures of tocopherol with approximately 40% by weight residual sterols and hydrocarbons.

A well known commercial activity is the conversion of tocopherol, and especially d-alpha-tocopherol, into a solid form for convenient human consumption. One of the best methods commercially used to solidify tocopherol is to prepare tocopheryl succinate. Typically, tocopheryl succinate is prepared by reacting tocopherol with succinic anhydride, and then isolating the half ester product by crystallization. References describing methods of this nature are described in U.S. Pat. No. 3,538,119 and in British Patent No. 866,489. Another reference which describes both the preparation of alpha-tocopheryl succinate and its recovery is British Patent No. 1,114,150.

For medicinal and health applications requiring tocopherol, solid tocopherol derivatives are prepared. It is desired that such tocopherol derivatives be capable of dissolving in an aqueous solution and be highly potent with a high degree of vitamin E biological activity per unit. The preparation of tocopherol derivatives is described in U.S. Pat. No. 2,680,749, which describes, as a preferred method, reacting tocopherol with a suitable polybasic acid anhydride such as succinic acid anhydride under usual esterification conditions.

Tocopheryl succinate, which is a vitamin E, melts at about 73°–78° C. It is a white solid material which at room temperature is waxy and tacky and which has poor flow properties. Furthermore, the commercially available tocopheryl succinate ordinarily has a broad particle size distribution with many fine particles which causes the powder to be cohesive and to form lumps.

A number of attempts have been made to prepare free-flowing tocopheryl succinate with and without additives. A prior art method is disclosed in U.S. Pat. No. 3,551,457. In this method tocopheryl succinate is heated to melt it, i.e., to about 85° C., and the melt is poured into a shallow pan so as to form a layer having a thickness of between 0.3 and 2.5 cm, after which the melt is allowed to harden and crystallize over a period of 12–24 hours. The resulting mass is then ground at a low temperature, preferably at a temperature of about −80° C.

British Patent No. 1,007,161 discloses another method of preparing free-flowing, powdered tocopheryl succinate having a high bulk density. In the method tocopheryl succinate is melted and the melt is dispersed in an aqueous solution containing a thickening agent in the form of methyl cellulose, and subsequently the dispersion formed is quickly cooled so as to cause the tocopheryl succinate to crystallize to form fine particles which are separated and dried. A product thus prepared has a relatively broad particle size distribution which causes problems in the treatment of the product in known tabletting machines. Furthermore, the use of methyl cellulose as thickening agent results in a certain tackiness which imparts to the product a tendency to, adhere to e.g., parts of the tabletting machine.

U.S. Pat. No. 4,870,196 (Thorengaard) discloses a method of preparing powdered, free-flowing tocopheryl succinate having a high bulk density comprising melting a mixture of tocopheryl succinate and wax, spraying the melt in a spraying zone containing a cloud of a powdering agent consisting of fine tocopheryl succinate and an additional powdering agent, and maintaining the product formed in a fluidized state by introducing cooling air until the tocopheryl succinate particles have hardened, and separating the product formed into a product fraction and a fine fraction, and recycling the fine fraction to the spraying zone.

Thorengaard reports that attempts to prepare tocopheryl succinate in the form of particles coated with other agents than the ones described above have not produced satisfactory results as these attempts have resulted in the reduction of the tocopheryl succinate content of the final product. It is stated that this is undesirable because of the subsequent preparation of high-dosed capsules and tablets since for such use it is desirable that the starting material contains as much tocopheryl succinate as possible and that it also has a high bulk density.

SUMMARY OF THE INVENTION

This invention relates to a method of producing a tocopheryl succinate comprising heating a mass of tocopheryl succinate to an elevated temperature to form a plastic mass and cooling said mass to allow said mass to set to a solid form. The elevated temperature is low enough that the entire mass is not melted. Thus, the temperature of the entire mass will not exceed the melting point of tocopheryl succinate. The mass is typically divided into discrete portions, e.g. multiple ropes of extrudate, prior to being allowed to set. The mass of tocopheryl succinate is preferably essentially free of added binders, e.g. natural or synthetic polymers that are added thereto.

DETAILED DESCRIPTION OF THE INVENTION

This invention relates to a method for increasing the particle size of tocopheryl succinate. The starting tocopheryl succinate is a solid material and at no point in this process of size enlargement is the mass of tocopheryl succinate heated above the melting point of tocopheryl succinate so as to melt the entire mass of material. Thus, the plastic mass of tocopheryl succinate is a shapeable, e.g. moldable or extrudable, material as opposed to a fully liquid melt. The product of the process is, in a sense, agglomerated particles of tocopheryl succinate because the process may be characterized as an agglomeration process.

In typical embodiments, the process can be characterized as extrusion of a plastic mass of powdered tocopheryl succinate (e.g. the starting powder having a substantial portion, e.g. at least 5% by weight, of particles capable of passing through an 80-mesh (U.S. standard) sieve) wherein the temperature of the powder is sufficient to plastify the mass, but insufficient to melt all of the solid particles of said tocopheryl succinate. The tocopheryl succinate to be used in the practice of the invention is typically in the free acid form. However, pharmaceutically acceptable salts, e.g. the sodium or potassium salts may also be useful.

The tocopheryl succinate used as a starting material in this invention is, typically, initially in the form of a powder. The term "powder", without further express limitation, denotes only that the product consists essentially of particles having a relatively small average particle size, e.g. an average particle size of less than about 1 millimeter. Typically, the tocopheryl succinate will have essentially no particles (i.e. at most a trace amount) retained on an 14-mesh (U.S. standard) sieve (i.e. having openings of 1.4 millimeters).

The tocopheryl succinate is preferably free of added binders. Examples of binders include water-soluble celluloses, pregelatinized starches, and water-soluble macromolecules. The water-soluble celluloses include hydroxypropylcellulose, hydroxymethylcellulose, hydroxypropylmethylcelulose, carboxymethylcellulose and methylcellulose. A pregelatinized starch is a product obtained, for example, by heating a dispersion of starch in water, followed, as desired, by drying. Examples of water-soluble macromolecules includes polyvinylpyrrolidone (e.g. M.W. 10,000–100,000), polyvinyl alcohol (e.g. M.W. 10,000–50,000), dextrin, gum arabic, gum acacia, and gelatin. The tocopheryl succinate is also typically essentially free of solvents such as water or organic solvents, e.g. alcohols (e.g. methyl alcohol, ethyl alcohol, isopropyl alcohol) and ketones (e.g. acetone) and hydrocarbons, (e.g. hexane).

The tocopheryl succinate powder is subjected to sufficient heat and pressure to render it plastic. However, the temperature must be low enough that the entire mass does not melt. Without wishing to be bound by any particular theory, unless otherwise expressly noted, it is believed that the predominant portion by weight of the mass remains as solid particles, but that these particles are mixed with a phase of the tocopheryl succinate that is rendered fluid as a result of the heat and/or pressure. Upon exit of the resulting plastic mass from the zone of heat and/or pressure, the fluid phase reverts to solid form much more quickly than a fully melted liquid of tocopheryl succinate.

An extruder has been found to be particularly useful in forming and shaping the plastic mass of tocopheryl succinate. Extruders are generally described in *Encyclopedia of Polymer Science and Engineering*, vol. 11, pp. 262–267 (John Wiley & Sons, Inc., N.Y., N.Y. 1988) the disclosure of which is incorporated herein by reference. The extruders useful herein may vary. Although single screw extruders can be employed, preferred extruders are the twin screw extruders of which the co-rotating twin screw extruders are especially preferred. Of particular interest are the so-called "cooker extruders" which provide for heating of the materials which are introduced within the extruder. Various screw configurations can be employed. For example, screws having combinations of elements for feeding, mixing, pumping, shearing, and the like, can be selected as desired for optimum results. Screws having sections or elements which provide relatively large output capacities, which have interrupted or nonconjugated flights, or which are "counter-flighted" or "reversing" also can be employed. Typical screw elements as well as screws having combinations of such elements are available from extruder manufacturers. The length to diameter ratio of the extruder will typically range from about 10:1 to about 50:1.

The plastic mass is typically divided into discrete portions, typically by passage through a die having a plurality of openings therein. Thus, dies for practicing the invention have a multiplicity of very small die openings or holes. All openings for any one die are preferably of equal size (i.e. equal in area dimension). The openings may vary from about 0.1 to about 4 millimeter diameter for different dies. Square or multi-sided openings may be used, but ideally, the openings are circular to give a cylindrical shape to resulting extrusions. The die is preferably oriented in a horizontal plane for vertical passage through the die. Such vertical discharge helps to prevent the initial material through the die from fowling the die openings. A heated die plate, i.e. one heated to the temperature of the last extruder zone, is also preferred.

A particularly useful extruder is the Wenger TX-52 extruder, commercialized by Wenger Manufacturing, Inc. of Sabetha, Kans., provided with two rotatable, flighted material advancing screws (screw elements of 52-mm diameter) with a total of 5 barrel sections and terminated in a spacer plate die. The screws will typically be inter-meshing and co-rotating. The die plate typically will have six die inserts, typically arranged in a hexagonal design, with a number of holes of the desired diameter in each insert, typically from 25 to 100 holes, each hole typically having a diameter of 0.1 mm to about 2 mm, preferably from about 0.4 mm to about 0.6 mm. The design of the Wenger TX line of extruders is described in U.S. Pat. No. 4,875,847, which is incorporated by reference herein. The extruder is designed to heat the contents thereof and to expose the contents to significant compaction and shear. The temperature of the contents of the extruder should be maintained sufficiently low such that the entire mass of tocopherol succinate is not fully melted. Thus, the temperature of the entire contents of the extruder should not be allowed to exceed a temperature of about 72° C. Typically, the temperature of the mass will be below about 70° C., more typically below about 65° C. Typically, the tocopheryl succinate will be fed into the extruder at ambient, and will be gradually heated to a temperature of about 55° C. to about 65° C., more typically to a temperature of about 60° C. to about 63° C., just prior to exit of the material from the extruder. With a five section extruder, the set temperature of the heating medium will typically be about 45° C. to about 55° C., in the first two sections (e.g. contents in these two sections typically at about 30° C. to about 35° C.), about 50° C. to about 60° C. in the third and fourth sections (e.g. contents in third section typically about 52° C. to about 56° C. and in the fourth section about 55° C. to about 60° C.) and about 58° C. to about 62° C. in the last section (e.g. contents in last section about 60° C. to about 62° C.). It may be desirable to expose portions of the plastic mass to, e.g. that portion of the mass in contact or close proximity with the interior wall of the barrel of the extruder or the die plate, to temperatures that are in excess of 72° C., e.g. about 75° C., to provide lubrication of the wall or die plate. In such a case, however, one should ensure that the entire mass will not reach a temperature above about 72° C. The product will typically be fed to an extruder such as the Wenger TX-52 at a rate of about 70 to 75 kg/hr and the screw speed will typically be between about 160 rpm and 165 rpm.

The product of the extrusion will be a material which, upon cooling, sets to form a solid product within a matter minutes, typically less than about 1 hour, more typically at most about 30 minutes, and more preferably at most about 10 minutes. Preferably, the mass sets to a solid form in a matter of a few seconds, typically from about 1 second to about 30 seconds. It has been found that the material which takes a relatively longer time to set (which typically results when the plastic mass is heated to a relatively high temperature) appears to be harder after set than the material which sets more quickly. The material which sets more quickly is thus, more fragile and friable than the material which takes a longer time to set.

The extrudate will typically be in the form of a rope or plurality of ropes which can then be subjected to size reduction to obtain a product having the desired particle size. Size reduction is discussed in *Encyclopedia of Chemical Technology*, vol. 21, pp. 132–162 (John Wiley & Sons, Inc., N.Y., N.Y. 1983) the disclosure of which is incorporated herein by reference. The apparatus chosen for size reduction is preferably one which accomplishes size reduction by impact, and with minimal, if any, shear or compaction. Examples of preferred size reduction apparatus include a disk mill or pin mill. In such mills, the tocopheryl succinate will come into contact with striking members, e.g. bars or pins, attached perpendicularly to the plane of a rotating member, e.g. a disk or plate. The impact of the tocopheryl succinate will cause a reduction in the size of the particles thereof. There is preferably no surface in contact with or within close tolerance of the striking members so that there will be little of no shear or compaction, as opposed to free impact, applied to the particles. The chamber of such a mill is typically bounded with a screen with openings therein which will allow material of the desired size to exit the chamber therethrough. An example of a preferred impact mill is the model SM-18 Prema Mill, Prater Industries, Inc., Chicago, Ill. Such a grinder can typically produce about 60 pounds/hr when operated at a tip speed of 10 meters/second.

In preferred embodiments, the extrudate will be in an elongated form, e.g. ropes, which have an axial dimension of roughly the size desired of the powdered particle, e.g. from about 0.4 mm to about 0.6 mm. Thus, the size reduction will serve largely to reduce the elongated dimension of the ropes to roughly the size of the axial dimension. Of course, the size reduction process will also serve to break the particles through the axial dimension as well, so that the average diameter of the resulting product will be less than the axial dimension of the elongated starting material.

During size reduction, the tocopheryl succinate should be maintained below the melting point of the product, preferably at or below ambient temperature of about 25° C. Cooling air or other cooling fluid, e.g. liquid nitrogen, can be introduced into the milling chamber to cool the product during size reduction.

In typical operation, the process will entail dropping fine tocopherol succinate powder into a feeder which in turn feeds the powder to an extruder at a controlled rate. The extruder heats the powder with shear and pressure to form a flowable material that is not fully melted. The pressure generated by the extruder forces the flowable material through die openings at the end of the extruder barrel. Upon exiting the extruder, the extruded material is vertically discharged onto a belt. The belt conveys the extruded material for sufficient time for the material to harden to a solid form. The hardened material then falls off the end of the belt into coarse crushing wheels which break the strands of extrudate into shorter, but still elongated pieces. The reduced material falls into a holding bin prior to falling into a feeder. The feeder then feeds the reduced material to a grinder at a controlled rate. The grinder is cooled to prevent material from melting. The grinder reduces the particle size of the material to a desired range. The ground material is then screened to remove particles considered too large (e.g. those retained on a 14-mesh screen) and too small (those passed by a 120-mesh screen). The material which is too small can be added to the feed of the extruder and the material which is too large can be added to the feed of the grinder.

The product can be characterized as a powdered composition. If desired, it can be sieved in order to obtain a desired grain size distribution. An excessively fine composition is undesirable because of its poor flowability in charging into dies in tabletting. An excessively coarse composition is unsuited for admixture with some other composition and moreover causes weight fluctuation in tablet manufacture. A typical lower limit on grain size is typically a maximum of 5% by weight of the grains through a 120-mesh sieve. Typically, the product will have less than 5% retained on a 14-mesh sieve. Preferably at least about 85% of the material will pass a 25-mesh sieve, but will be retained on a 60-mesh sieve.

The mesh sizes as defined in this specification are those specified in the relevant U.S. standard (as published in *Handbook of Chemistry and Physics*, p. F-158 (57 the ed., CRC Press, Cleveland Ohio, 1976)). Said mesh sizes and the corresponding sieve opening sizes are shown below.

| Mesh | Sieve opening size (micrometers) |
| --- | --- |
| 10 | 2,000 |
| 20 | 850 |
| 80 | 180 |
| 120 | 125 |

The tocopheryl succinate according to the invention can be used as a raw material in the manufacture of tocopheryl succinate-containing tablets and capsules. Tabletting of the powder is carried out by a conventional method in the presence of a lubricant and, if necessary, some other drug substance and/or an excipient (e.g. lactose, sucrose, mannitol). As said lubricant, there may be mentioned those lubricants which are used in conventional tablet manufacture, such as stearic acid and stearates (e.g. magnesium stearate, calcium stearate) and talc. The amount and kind of the lubricant are selected within such a range as to give tablets which are practical from the strength and disintegration viewpoint. Typically, it is used in an amount of about 0.1 to about 7 percent by weight based on the main active substance. Of the lubricants, a stearate or stearic acid is typically added in an amount of at least about 0.5 percent by weight based on the main active substance. The above-mentioned other drug substance can include a variety of vitamins, mineral, and other dietary supplements. The compression is normally carried out under the condition of 1 to 2 ton/cm$^2$.

The following examples will illustrate the invention and should not be construed to limit the invention, except as expressly noted in the appended claims. All parts, ratios and percentages stated herein are by weight unless noted otherwise in context.

EXAMPLES

Tocopheryl succinate powder (available from Henkel Corp., Ambler, Pa., as Covitol 1210) is charged to a Wenger TX-52 extruder. The extruder had five barrel sections, the set temperature and actual temperature of the contents of each section being set forth below. The die consisted of a die plate with six inserts each having 61 openings, each opening 0.5 mm in diameter. A 90° elbow was attached to the end of the extruder. A six insert die plate was attached to the end of the elbow. Throughout the trial Covitol 1210 was used as the feed for the extruder. The extruded material was discharged vertically. The 0.5 mm die inserts were the only inserts used during the trial. The running conditions of the trial are listed in the following Table 1.

TABLE 1

| Run | 1 | 2 | 3 |
|---|---|---|---|
| Feed Screw Spd. (rpm) | 20 | — | — |
| Extruder Shaft Speed (rpm) | 100 | 162 | 175 |
| Extr. Motor Load (%) | 24 | 31 | 30 |
| Zone #1 Set/Act. (°C.) | 50/38 | 50/32 | 50/32 |
| Zone #2 Set/Act. (°C.) | 50/38 | 50/32 | 50/32 |
| Zone #3 Set/Act. (°C.) | 55/57 | 55/56 | 55/56 |
| Zone #4 Set/Act.(°C.) | 60/60 | 60/60 | 60/60 |
| Zone #5 Set/Act. (°C.) | 60/60 | 60/61 | 60/61 |
| Die Config. & Dia. | 6 × 61 × 0.5 mm | 6 × 61 × 0.5 mm | 6 × 61 × 0.5 mm |
| Total Die Opening (cm$^2$) | 2.875 | 2.875 | 2.875 |
| Zone #4 Press. (kPa) | 0 | 4830 | 4830 |
| Zone #5 Press. (kpa) | 5170 | 6210 | 6210 |
| Rate (kg/hr.) | 36 | 72 | 78 |

The product of the run 2 of the above extrusion was then ground in a Prema SM-18 impact mill, Prater Industries, Chicago, Ill. For each run the material was loaded into a bin and fed into the grinder using a vibrating feeder. The screen surrounding the impeller had holes of approximately 2.4 mm. (This size is larger than the particles which pass through the screen because the angle at which the particles typically approach the screen causes the apparent diameter of the holes to be smaller than 2.4 mm.) The running conditions and screening results of each trial are listed in Table 2.

TABLE 2

| Run # | 1 | 2 | 3 |
|---|---|---|---|
| Rotor Tip Speed (m/s) | 10 | 16 | 27 |
| No Load/Run Load (amps) | 0.6/0.8 | 0.6/1.0 | 1.0/2.3 |
| Feed Rate (lbs/hr) | 60 | 112 | 112 |
| % on 14 Mesh Screen | — | — | — |
| % on 25 Mesh Screen | 5.4 | 2.1 | 0.4 |
| % on 30 Mesh Screen | 31.8 | 13.2 | 7.2 |
| % on 40 Mesh Screen | 53.3 | 43.8 | 50.8 |
| % on 60 Mesh Screen | 8.4 | 38.5 | 33.3 |
| % on 120 Mesh Screen | 0.2 | 0.9 | 3.0 |
| % on 140 Mesh Screen | — | 0.3 | 1.4 |
| % Less Than 140 Mesh Screen | 0.2 | 1.2 | 3.5 |

What is claimed is:

1. A process for increasing the particle size of a powder comprising tocopheryl succinate without binders, which comprises the steps of:

heating a mass of tocopheryl succinate powder to an elevated temperature effective to form a plastic, but not melted, mass of tocopheryl succinate;

extruding said mass into at least one elongated form;

allowing said elongated form to cool for an effective period of time to set to a solid form; and reducing the particle size of said solid form.

2. The process of claim 1 wherein said elevated temperature does not exceed about 72° C.

3. The process of claim 1 wherein said elevated temperature is below about 70° C.

4. The process as claimed in claim 1 wherein said elevated temperature is from about 60° C. to about 65° C.

5. The process of claim 1 wherein said heating is accomplished with an extruder.

6. The process of claim 1 wherein said elongated form is a rope having an axial dimension of about 0.1 mm to about 2 mm.

7. The process of claim 1 wherein said elongated form is a rope having an axial dimension of about 0.4 mm to about 0.6 mm.

8. The process of claim 1 wherein said plastic mass sets to a solid form within one hour of the beginning of said cooling of said plastic mass.

9. The process of claim 1 wherein said plastic mass sets to a solid form within about 30 minutes of the beginning of said cooling of said plastic mass.

10. The process of claim 1 wherein said plastic mass sets to a solid form within about 10 minutes of the beginning of said cooling said of plastic mass.

11. The process of claim 1 wherein said plastic mass sets to a solid form in less than about 30 seconds.

12. The process of claim 1 wherein said plastic mass sets to a solid form in about 1 second to about 30 seconds.

13. The method of claim 1 wherein said reducing consists essentially of impacting said form.

14. The process of claim 1 wherein said reducing does not compact the particles of said mass in solid form.

15. The process of claim 1 wherein said reducing is accomplished in an impact mill wherein there is no contact of the impacting impact members of said mill with an opposing surface of said mill.

16. The process of claim 1 Wherein the product of said reducing has a particle size such that a maximum of 5% by weight passes through a 120-mesh sieve.

17. The process of claim 1 wherein the product of said reducing has a particle size such that less than 5% by weight will be retained on a 14-mesh sieve.

18. The process of claim 1 wherein the product of said reducing has a particle size such that at least about 85% of the material will pass a 25-mesh sieve, but will be retained on a 60-mesh sieve.

* * * * *